(12) United States Patent (10) Patent No.: US 8,058,057 B2
Cattadoris et al. (45) Date of Patent: Nov. 15, 2011

(54) CELL CULTURE APPARATUS AND METHOD

(75) Inventors: Henry J. Cattadoris, Scarborough, ME (US); Martin J. Popoloski, Lowell, MA (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 314 days.

(21) Appl. No.: 12/241,522

(22) Filed: Sep. 30, 2008

(65) Prior Publication Data

US 2009/0298180 A1 Dec. 3, 2009

Related U.S. Application Data

(60) Provisional application No. 61/130,400, filed on May 30, 2008.

(51) Int. Cl.
*C12M 1/00* (2006.01)
*C12M 3/00* (2006.01)

(52) U.S. Cl. .................. 435/294.1; 435/304.2; 366/275

(58) Field of Classification Search ............... 435/264.1, 435/383; 366/275, 333, 349; 210/122
See application file for complete search history.

(56) References Cited

U.S. PATENT DOCUMENTS

| | | | |
|---|---|---|---|
| 3,948,732 A | 4/1976 | Haddad et al. | 195/127 |
| 4,539,005 A * | 9/1985 | Greenblatt | 604/141 |
| 4,661,455 A | 4/1987 | Hubbard | 435/240 |
| 5,523,228 A | 6/1996 | Ingram et al. | 435/240.25 |
| 5,896,641 A | 4/1999 | Yamada et al. | 29/455.1 |
| 5,975,636 A | 11/1999 | Koch et al. | 297/354.13 |
| 6,048,723 A | 4/2000 | Banes | 435/305.1 |
| 6,057,150 A | 5/2000 | Lee et al. | 435/288.3 |
| 6,468,792 B1 | 10/2002 | Bader | 435/325 |
| 6,586,235 B1 | 7/2003 | Banes | 435/293.1 |
| 6,637,437 B1 | 10/2003 | Hungerford et al. | 128/898 |
| 2001/0021530 A1 | 9/2001 | de Bruijn et al. | 435/395 |
| 2003/0082069 A1 * | 5/2003 | Kuzyk | 422/1 |
| 2004/0062140 A1 | 4/2004 | Cadogan et al. | 366/144 |
| 2004/0208761 A1 | 10/2004 | Bader | 417/417 |
| 2004/0219659 A1 | 11/2004 | Altman et al. | 435/284.1 |
| 2005/0002910 A1 | 1/2005 | Wolfinbarger et al. | 424/93.7 |
| 2005/0063250 A1 | 3/2005 | Hubbard | 366/275 |
| 2005/0267596 A1 | 12/2005 | Chen et al. | 623/23.67 |
| 2006/0270023 A1 | 11/2006 | LeDuc et al. | 435/289.1 |
| 2007/0080981 A1 * | 4/2007 | Karppinen et al. | 347/22 |

FOREIGN PATENT DOCUMENTS

| | | |
|---|---|---|
| WO | WO00/34442 | 6/2000 |
| WO | WO02/46365 | 6/2002 |
| WO | WO2006/072911 | 7/2006 |

OTHER PUBLICATIONS

"Flexcell Culture System", Flexcell International Corporation, pp. 1-5.

* cited by examiner

*Primary Examiner* — William H Beisner
*Assistant Examiner* — Michael Hobbs
(74) *Attorney, Agent, or Firm* — Susan S. Wilks; Thomas R. Beall

(57) ABSTRACT

A cell culture apparatus includes a housing, a bag and an inflatable bladder. The bag is disposed in the housing and has an interior surface defining a chamber for culturing cells. The bladder is disposed in the housing, external to the bag, and is sufficiently inflatable and expandable to exert pressure on the bag when the chamber is substantially free of fluid. The bladder may be inflated and expanded to reduce movement of the bag within the housing. Alternatively, or in addition, the bladder may be inflated and expanded to apply a mechanical stress on cells cultured within the chamber of the bag.

11 Claims, 12 Drawing Sheets

CELL CULTURE APPARATUS AND METHOD

CLAIMING BENEFIT OF PRIOR FILED U.S. APPLICATION

This application claims the benefit of U.S. Provisional Application Ser. No. 61/130,400, filed on May 30, 2008. The content of this document and the entire disclosure of publications, patents, and patent documents mentioned herein are incorporated by reference.

FIELD

The present disclosure relates to apparatuses for culturing cells; more particularly to apparatuses that contain a variable volume or fluid such as flexible, bag-type vessels.

BACKGROUND

Cell culture vessels containing flexible, bag-type cell culture chambers can be difficult to manipulate if they are not supported by a rigid housing. If the flexible, bag-type cell culture chambers are supported by a tight-fitting rigid housing, the housing must also adjust to accommodate the expanding bag as it fills. If the housing is constructed so that it has a fixed capacity, then an under-filled bag will be free to move about within the housing during transport or other manipulations.

Growing large numbers of attachment dependent cells in bag-like cell culture devices is very difficult because the bags are inherently flexible. This characteristic compromises the ability of the cells to attach and decreases the possibility that the vessel can be manipulated robotically. To grow large numbers of cells, a large surface area is needed. Increasing the surface area of a bag-like device complicates handling. Stacking several smaller bag-like vessels typically requires a separate unit with shelves upon which the vessels can be supported. If the vessels are stacked to form an integral unit, a fixed volume is usually necessary to provide a rigid support. This abolishes the variable-volume benefit of having a bag-like device.

Most cell types may be cultured in bag-like cell culture devices. For example, cells such as cardiac, lung, muscle, bone and cartilage cells may be culture in such devices. Such cells when grown in vitro under conditions where some type of mechanical stress is applied to the cultured cells, differentiate to phenotypically resemble their in vivo counterparts. Without such an applied stress, such cells typically require soluble factors to differentiate. To induce differentiation via mechanical stress and strain, many researchers cobble together their own devices to provide the physical stimulus required to encourage cells to differentiate along a particular lineage. Commercially available devices for application of mechanical stress and strain tend to be very precise and limited to very small numbers of cells in culture.

BRIEF SUMMARY

Devices and methods are described herein that employ an inflatable space-filling bladder within the housing of a cell culture apparatus. A bag for culturing cells is also disposed within the housing of the apparatus. The volume of the bladder may be altered in opposition to the cell culture vessel volume within the housing to aid in transport or manipulation of the device. In various embodiments, the bladder may be employed to apply compressive stress to cells cultured in the apparatus.

In an embodiment, a cell culture apparatus is disclosed. The apparatus includes a housing, a bag and an inflatable bladder. The bag is disposed in the housing and has an interior surface defining a chamber for culturing cells. The bladder is disposed in the housing, external to the bag, and is sufficiently inflatable and expandable to exert pressure on the bag when the chamber is substantially free of fluid. The bladder may be inflated and expanded to reduce movement of the bag within the housing. Alternatively, or in addition, the bladder may be inflated and expanded to apply a mechanical stress on cells cultured within the chamber of the bag.

In an embodiment, a cell culture apparatus is disclosed. The apparatus includes (i) a housing defining a chamber having a substantially fixed volume, (ii) one or more components disposed within the housing and configured to occupy a variable portion of the volume of the housing chamber, and (iii) a bladder disposed within the housing. At least one of the one or more components is a bag having an interior surface defining a cell culture chamber. The bag occupies a first volume of the housing chamber volume when the cell culture chamber of the bag is substantially free of fluid and occupies a second volume of the housing chamber volume when the cell culture chamber of the bag is substantially filled with fluid. The second volume is greater than the first volume. The volume of the bladder is adjustable between (i) a volume that occupies substantially all of the remaining volume of the housing chamber when the bag occupies the first volume and (ii) a volume that occupies substantially all of the remaining volume of the housing chamber when the bag occupies the second volume.

In an embodiment, a method for reducing movement of a bag defining a cell culture chamber within a housing of a cell culture apparatus is described. The method includes inflating a bladder disposed in the housing to exert pressure on the bag to prevent the bag from moving within the housing.

In an embodiment, a method for culturing cells in a bag disposed in a housing of a cell culture apparatus is described. The method includes deflating a bladder disposed in the housing to provide sufficient space within the housing to introduce cell culture fluid into the bag. The method further includes introducing cell culture fluid into the bag.

In an embodiment, a method for applying stress to cells cultured in a bag disposed in a housing of a cell culture apparatus is described. The method includes inflating a bladder disposed in the housing to exert pressure on the bag.

The culture apparatuses and methods described herein may have one or more advantages over previously described cell culture apparatuses that contain bag-type cell culture chambers disposed within a housing. For example, in various embodiments, the apparatuses and methods employ a space-filling bladder to reduce movement of components, including the bag, within the housing. The bladder, in various embodiments, may be employed to introduce compressive stress to cells cultured in the bag in a controllable and cost effective manner. These and other advantages will be readily understood from the following detailed descriptions when read in conjunction with the accompanying drawings.

Figure 1A:
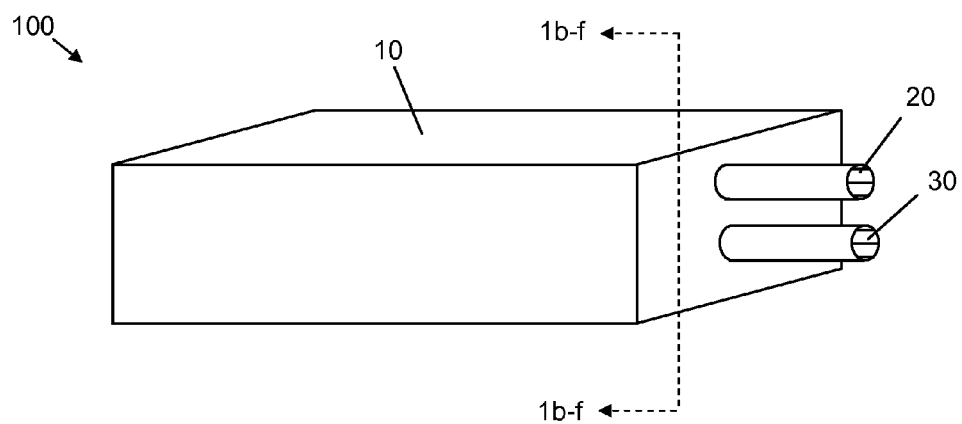
FIG. 1A is a schematic perspective view of a representative cell culture apparatus.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

The present disclosure describes, inter alia, cell culture apparatuses that employ an inflatable space-filling bladder within a housing of the apparatus. A bag for culturing cells is also disposed within the housing. The volume of the bladder may be altered in opposition to the cell culture vessel volume within the housing to aid in transport or manipulation of the device. Alternatively or in addition, the bladder may be employed to apply compressive stress to cells cultured in the apparatus.

Referring to FIGS. 1A-F, a schematic perspective view (1A) and schematic cross-sections (1B-D) of a representative cell culture apparatus are shown. The apparatus depicted in FIG. 1A includes a rigid housing 10, a bladder port 20 and a cell culture bag port 30. In various embodiments, the housing is formed from an optically transparent polymeric material, such as polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. In addition to the nature of the polymeric material selected, it will be understood that the rigidity of the housing 10 can be varied based on the thickness of the housing 10, and other factors known to those of skill in the art. In various embodiments, the thickness of the housing 10 is in a range between about 1 mm and about 2.5 mm. For example, the thickness of the housing may between about 1.5 mm and about 2 mm. In various embodiments, materials for forming the housing are selected to provide optical transparency.

The housing 10 may have any suitable dimensions. For example, the housing 10 may be 50 mm×75 mm in some embodiments and about 450 mm×775 mm in other embodiments.

Figure 1B:
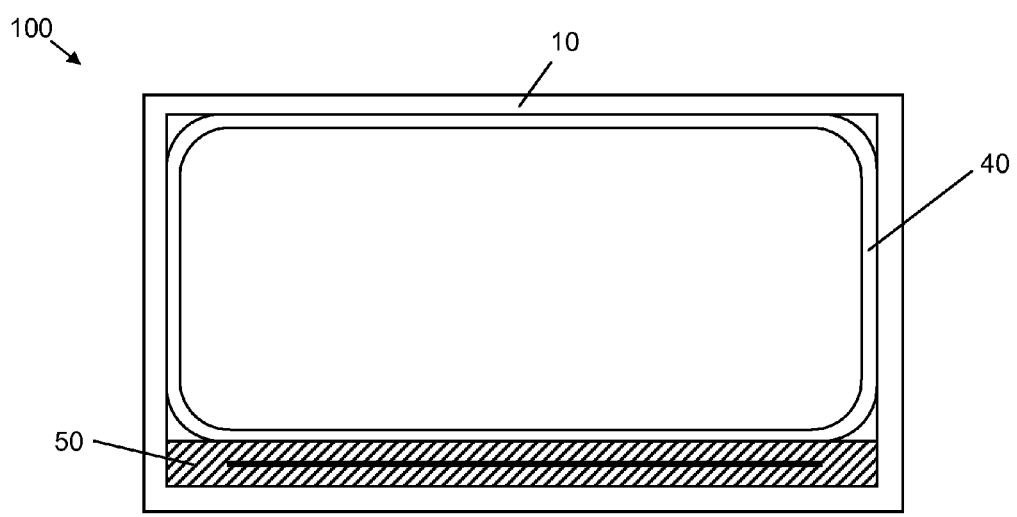
FIGS. 1B-F are schematic cross-sections of some representative components of the cell culture apparatus of FIG. 1A taken through line 1b-f-1b-f.
Figure 1C:
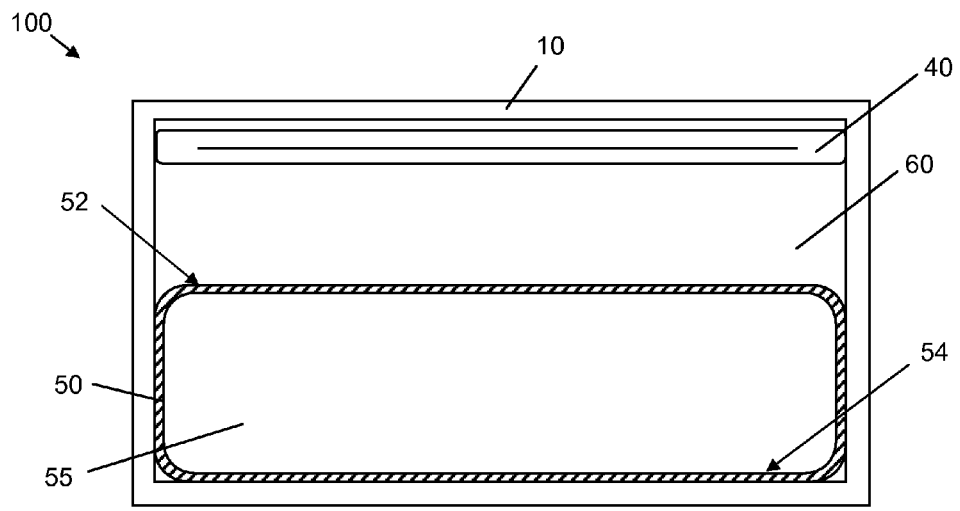
Figure 1D:
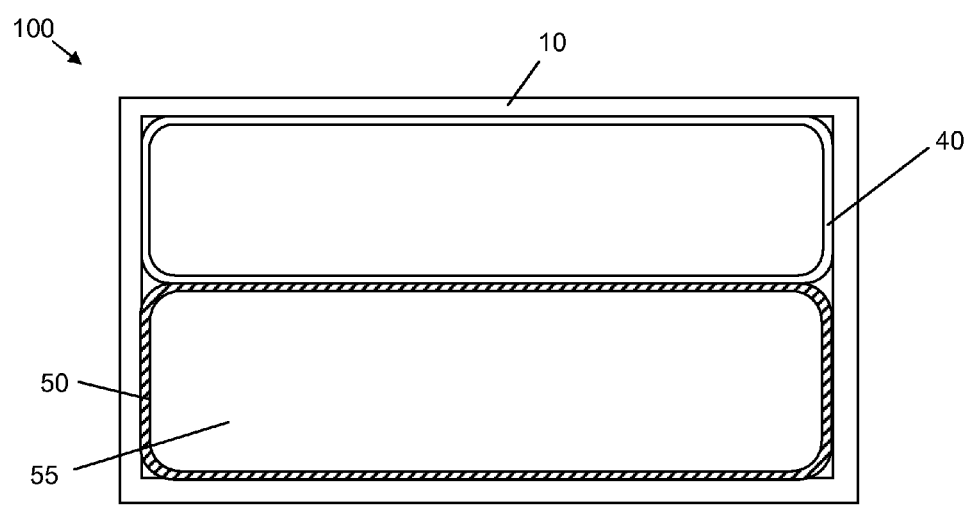
Figure 1E:
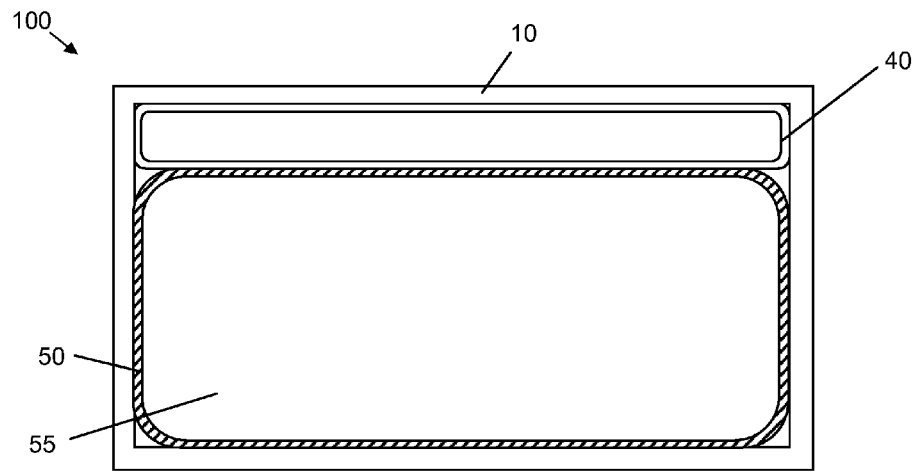

The bladder port 20 and the cell culture bag port 30 depicted in FIG. 1A extend through the housing 10 and allow access to an inflatable bladder 40 and a cell culture bag 50, respectively, disposed within the housing 10 (see, e.g., FIGS. 1B-D). The port may be made of any suitable material and may be rigid or flexible, or have rigid or flexible portions. Of course, it will be understood the bladder port 20 or the cell culture bag port 30 need not extend from the housing 10. In numerous embodiments, the bladder port 20 or the bag port 30 are openings (not shown) formed in the housing 10.

A septum, valve, cap (not shown) or the like may be disposed in or about a port 20, 30 to prevent unintended fluid leakage from the bladder 40 or bag 50. In various embodiments, the bladder port 20 of the bag port 30 are configured to be coupled to a pump (not shown in FIG. 1A) and may include connection fittings (not shown) to connect to the pump or to an adaptor for connecting to the pump. A port 20, 30 may be fluidly sealed with a bladder 40 or bag 50 through any suitable mechanism, such as, for example, heat sealing or RF welding.

Referring now to FIG. 1B, the cell culture bag 50 is depicted as empty and deflated; i.e. substantially free of fluid, such as cell culture fluid. The bladder 40 is inflated and exerts pressure on the bag 50. Such a configuration may be desirable for purposes of transport and handling of the cell culture article 100 prior to culturing cells in the article, as the inflated bladder 40 can limit movement of the culture bag 50 within the housing 10.

The bladder 40 may be made of any suitable of material that can be formed into an inflatable pouch, bag, or the like. For example, the bladder 40 may be formed from thin polymeric material or metal foil. In various embodiments, the bladder 40 is formed of optically transparent material to allow visual inspection of cells cultured in the culture bag 50, provided that culture bag 50 is also optically transparent. Examples of optically transparent materials that may be used to form the bladder 40 include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. The bladder 40 may be formed through heat sealing, laser welding, application of adhesive, or any other method known in the art of inflatable bag making. The bladder 40 may be expanded with a gas or liquid. A pump may be used to fill and remove the expansion gas or liquid, in conjunction with valves or mechanical occlusion to control the flow.

The culture bag 50 may be made of any suitable of material that can be formed into an inflatable pouch, bag, or the like in which cells may be cultured. In various embodiments, the bag 50 is formed of optically transparent material to allow visual inspection of cells cultured in the bag 50. Preferably, the bag 50 is gas permeable to allow exchange of gasses across the bag as cells are being cultured. Examples of optically transparent, gas permeable materials that may be used to form the bag 50 include polystyrene, polycarbonate, ethylene vinyl acetate, polysulfone, polytetrafluoroethylene (PTFE) or compatible fluoropolymer, a silicone rubber or copolymer, poly (styrene-butadiene-styrene), or polyolefin, such as polyethylene or polypropylene, or combinations of these materials. Preferably, the film 100 is of a thickness that allows for efficient transfer of gas across the film. It will be understood that desired thickness may vary depending on the material from which the film 100 is formed. By way of example, the film may be between about 0.02 millimeters and 0.8 millimeters thick. As with the bladder 40, the bag 50 may be formed through heat sealing, laser welding, application of adhesive, or any other method known in the art of inflatable bag making. Prior to sealing or forming the bag, it may be desirable to treat or coat that portion of the material in which cells will be cultured once formed. The treatment or coating may facilitate cell culture. Treatment may be accomplished by any number of methods known in the art which include plasma discharge, corona discharge, gas plasma discharge, ion bombardment, ionizing radiation, and high intensity UV light. Coatings can be introduced by any suitable method known in the art including printing, spraying, condensation, radiant energy, ionization techniques or dipping. The coatings may then provide either covalent or non-covalent attachment sites. Such sites can be used to attach moities, such as cell culture components (e.g., proteins that facilitate growth or adhesion). Further, the coatings may also be used to enhance the attachment of cells (e.g., polylysine). A pump, in conjunction with valves or mechanical occlusion to control the flow, may be used to fill and remove culture liquid, cells, or the like from the bag 50.

Referring now to FIG. 1C, the cell culture bag 50 is shown in an expanded state in which the bag contains fluid (not shown), such as cell culture liquid. The bag 50 has an external surface 52 and an internal surface 54. The internal surface 54 defines a variable volume chamber 55. As the bag 50 expands, the volume of the chamber 55 increases. The chamber 55 may be of any suitable volume for culturing cells. In various embodiments, the chamber 55 can expand to a volume of between about 0.1 ml/cm$^2$ and about 0.5 ml/cm$^2$ For example, the chamber 55 may expand to a volume of between about 0.2 ml/cm$^2$ and about 0.3 ml/cm$^2$.

The bladder 40 in FIG. 1C is shown in a deflated state such that it exerts substantially no pressure on the bag 50 containing fluid. As the bag 50 is filled, or before filling the bag 50, the bladder 40 may be deflated. It may be desirable to coordinate the filling of the bag 50 with the emptying of the bladder 40 such that spatial voids 60 in the housing 10 are minimized. For example and referring to FIGS. 1D-E, it may be desirable for the bladder 40 to deflate and contract to an amount substantially equal to an amount that the culture bag 50 inflates and expands. The coordination of the filling of the bag 50 and the emptying of the bladder 40 may be done manually and may include visual inspection, provided that the housing 10 is optically transparent. Alternatively or in addition, the coordination process may be automated (e.g. as described below with regard to FIG. 7). In some embodiment, the bladder 40 is in fluid communication with a pressure sensitive valve (not shown). The valve opens when pressure is exerted on the bladder 40 by the expanding bag 50 to allow fluid to escape the bladder 40 and allow the bladder 40 to contract. Whether controlled manually, automatically, or via a valve, the bladder 40 may be deflated such that it exerts any desired pressure on the expanding bag 50. In many embodiments, the bladder 40 exerts substantially no pressure (e.g., less than 0.1 psi or 7000 pascals) on the bag 40 cells are being cultured in the bag 50.

In some embodiments, fluid may be added to the bladder 40 to exert a pressure on the bag 50 when cells are being cultured. In such a manner a well-controlled mechanical and physical stress can be applied to the cells cultured in the bag 50. Certain types of cells, including cardiac, lung, muscle, bone and cartilage cells, when grown in vitro under conditions where some type of mechanical stress is applied to the cultured cells, differentiate to phenotypically resemble their in vivo counterparts. Whereas these cell types grown without an applied stress, require soluble factors to cause this differentiation. By using a bladder 40 to apply stress to cells cultured in a bag 50 as described herein, a large number of cells may be subjected to the stress, allowing for higher throughput analysis than previously achievable.

Figure 1F:
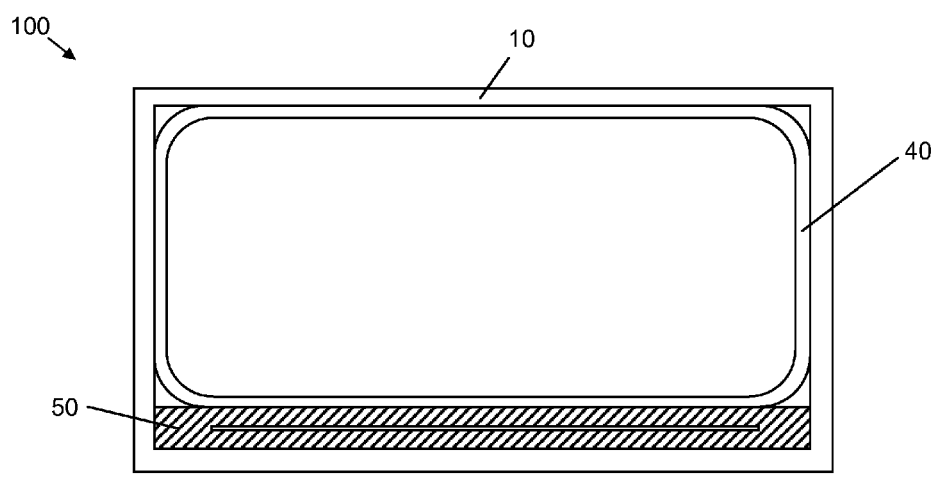

In various embodiments and referring to FIG. 1F, fluid may be added to the bladder 40 to exert pressure on the bag 50 to facilitate emptying of fluid from the culture bag 40.

Figure 2A:
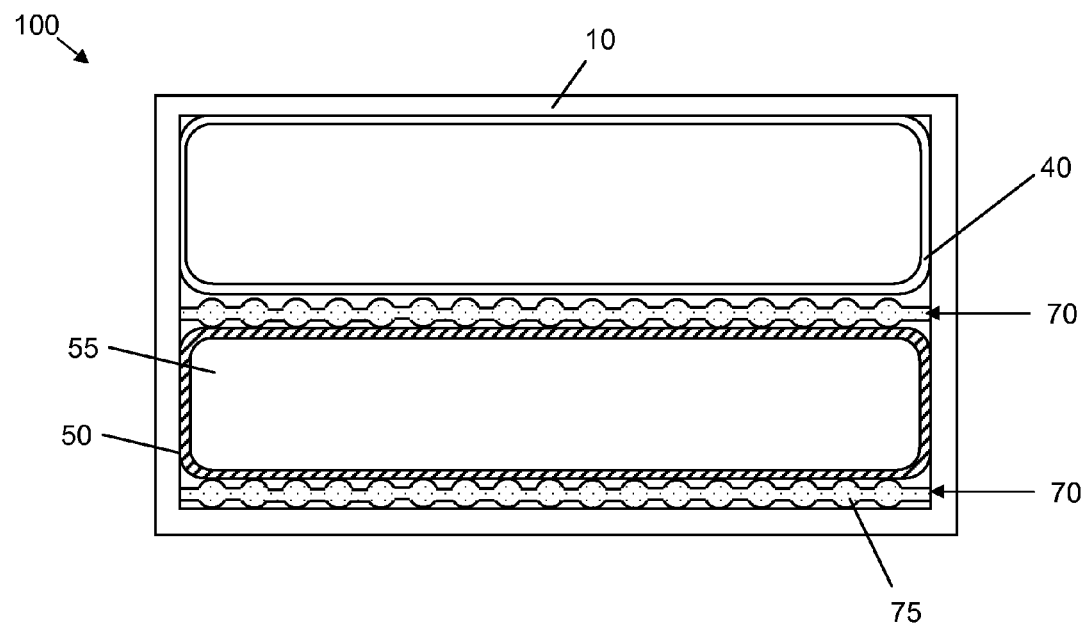
FIG. 2A is a schematic cross-section of some representative components of a representative cell culture apparatus.
Figure 2B:
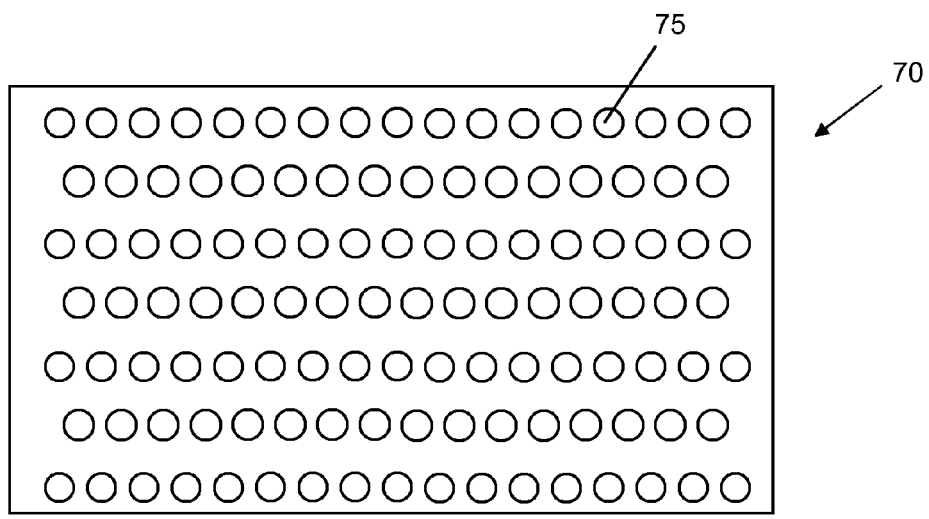
FIG. 2B is a schematic top view of a rigid shelf spacer depicted in FIG. 2A.

Referring now to FIG. 2, in which a schematic-cross section of a representative cell culture article 100 is depicted, the article 100 may include a spacer 70 to create air space for gas exchange across the bag 50. As such gas in the cell culture media within the chamber 55 may be exchanged with gas external to the bag 50 to maintain desirable culture conditions in the chamber 55. Preferably, spacers 70 are located on both sides of the bag 50 (i.e., the bag 50 is disposed between two spacers 70) to increase the surface area of air space in contact with the bag 50. However, it will be understood that a spacer 70 may be disposed only on one side of the bag 50 or no spacers 70 may be employed if sufficient exchange of air across the bag 50 is achieved for the intended cell culture purpose. Spacers 70 may take any suitable form, such as a woven mesh (not shown) or rigid shelves depicted in FIG. 2. Such rigid shelves may be molded or otherwise formed of nearly any suitable material, such as polymeric material. The molded shelves may include a plurality of raised features 75 to generate a large surface area of air space in contact with the exterior surface of the bag 45. A top view of a spacer shown in FIG. 2A is depicted in FIG. 2B.

In numerous embodiments, gas is exchanged between the cell culture chamber 55 and the exterior of the housing 10 via a passageway formed between spacers 70 and bag 50. In some embodiments, housing may be formed from gas-permeable material, such as polystyrene polystyrene, polyethylene, polycarbonate, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. The thickness of housing 10 may be varied to alter the gas-permeable properties of the housing 10. However, housing 10 should be sufficiently thick to maintain sufficient rigidity.

Figure 3:
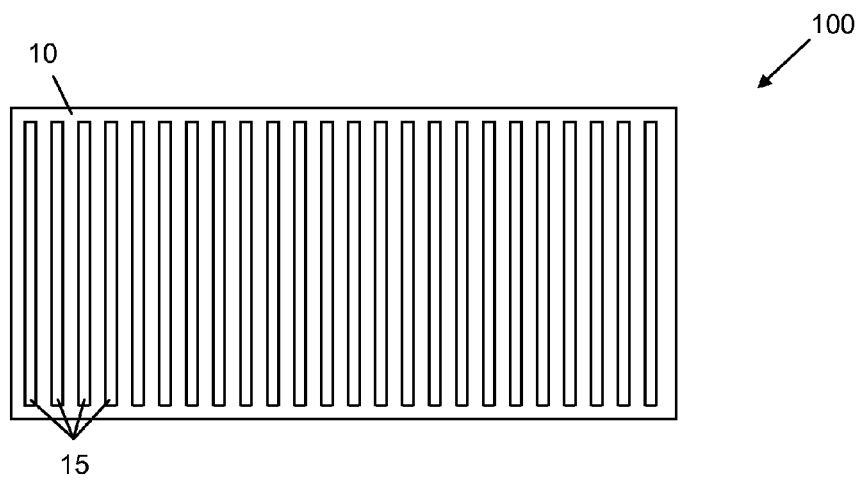
FIG. 3 is a schematic side view of a vented housing of a representative cell culture apparatus.

Alternatively or in addition, and with reference to FIG. 3 which depicts a schematic of a side view of a representative cell culture article 100, housing 10 may be formed with a series of openings 15 that may take the form of slots, holes, or the like. One or more of the openings 15 are in fluid communication with the passageway formed between spacer 70 and cell culture bag 50 (see, e.g., FIG. 2A).

Figure 4A:
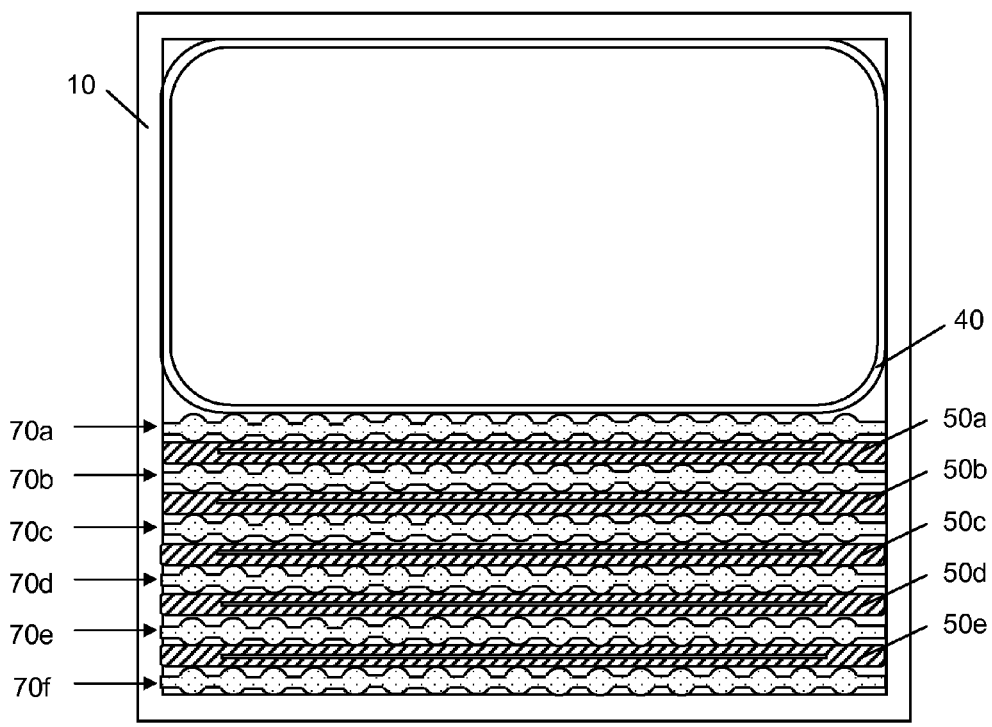
FIGS. 4A-C are schematic cross-sections of some representative components of a representative cell culture apparatus.
Figure 4B:
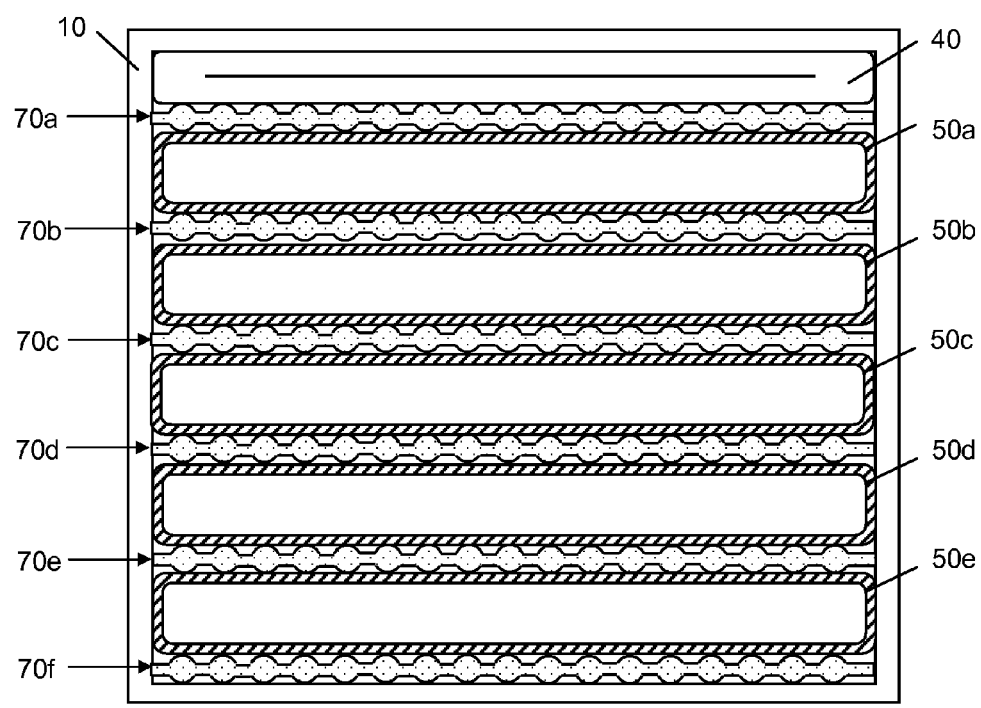
Figure 4C:
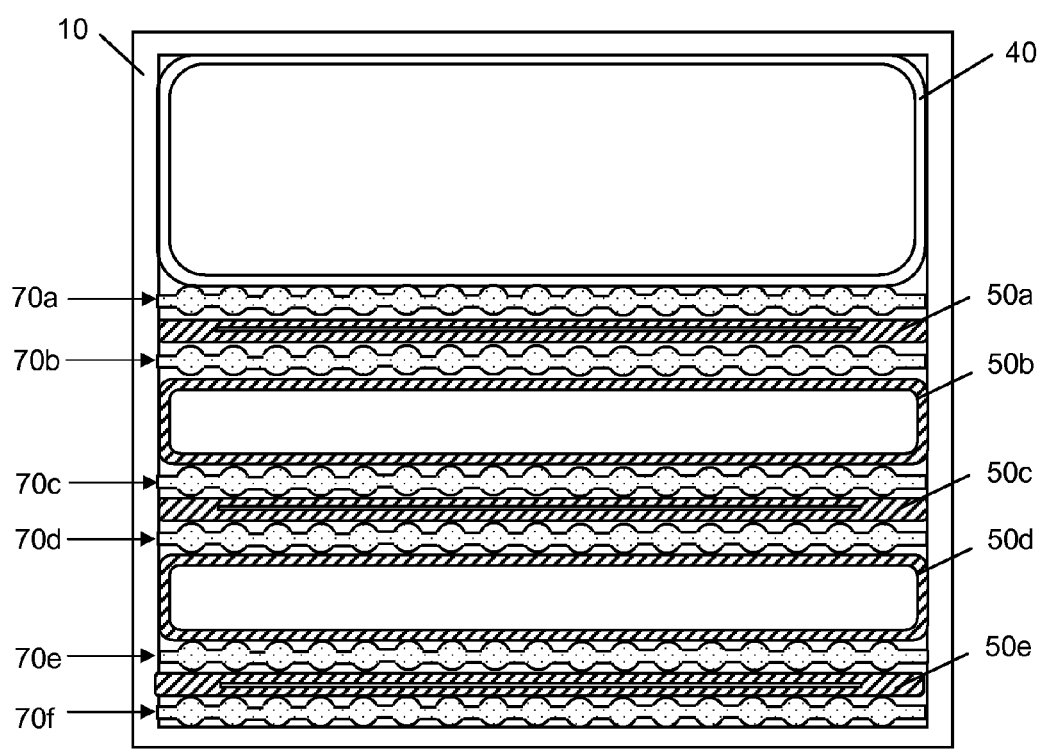

Referring now to FIGS. 4A-C, schematic cross-sections of a representative cell culture apparatus are shown. In the depicted embodiments, the article includes a plurality of cell culture bags 50*a-f* and a plurality of spacers 70*a-f*, shown in the form of rigid shelves, disposed between the bags 50*a-f*. A spacer 70*a* is disposed between the bladder 40 and the bag 50*a* closest to the bladder 40. A spacer 70*f* is disposed between the bottom of the housing 10 and the bag 50*e* disposed closest to the bottom of the housing 10. As discussed above, e.g. with regard to FIG. 1B, the bladder 40 may be inflated to exert pressure on the bags 50*a-e* and spacers 70*a-f* to prevent the bags 50*a-e* and spacers 70*a-f* from shifting within the rigid housing 10. The bladder 40 is sufficiently inflatable and expandable to exert pressure on the bags 50*a-e* and spacers 70*a-f* when the bags are substantially free of fluid, as shown in FIG. 4A. The bladder 40 sufficiently deflatable and contractible to allow bags 50*a-e* to expand when filled with fluid (see, e.g., FIG. 4B). The bladder 40 may exert any suitable level of pressure on the bags 50*a-e* when cells are being cultured in the bags 50*a-e*. For example, the bladder 40 may exert substantially no pressure on the bags 50*a-e* or may exert a sufficient amount of pressure to cause cells within the bags 50*a-e* to experience a desired mechanical or physical stress. In some embodiments, the bags 50*a-e* are capable of being filled or emptied individually. For example and referring to FIG. 4C, bags 50*b* and 50*d* are shown as filled with fluid. It will be understood that, as used herein, "filled" means filled to capacity or filled to partial capacity. In various embodiments, the bags 50*a-e* and spacer shelves 70 occupy less than half (e.g. about one-third) of the interior volume of the housing 10 when the bags 50*a-e* are empty and occupy greater than half (e.g. greater than about two thirds) when the bags 50*a-e* are filled.

Figure 5A:
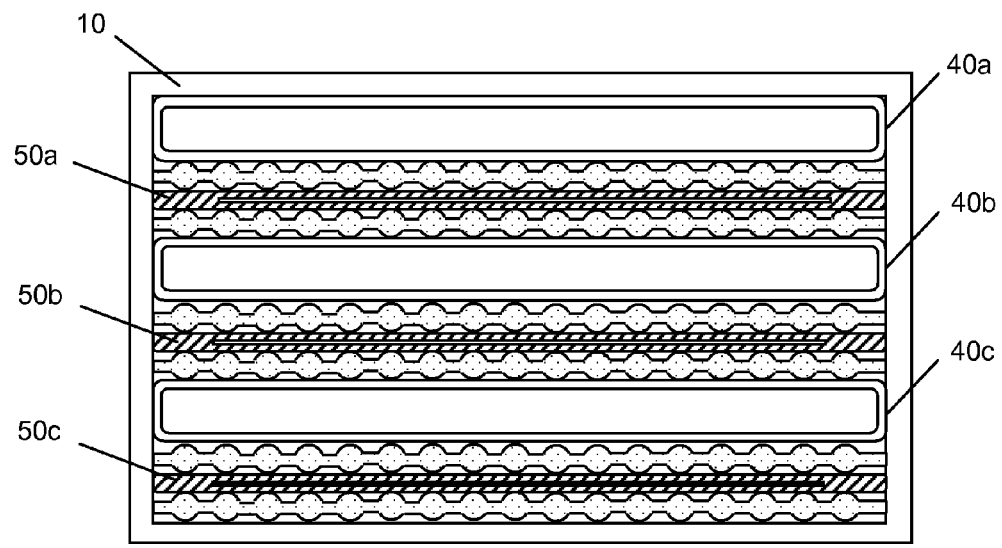
FIGS. 5A-B are schematic cross-sections of some representative components of a representative cell culture apparatus.
Figure 5B:
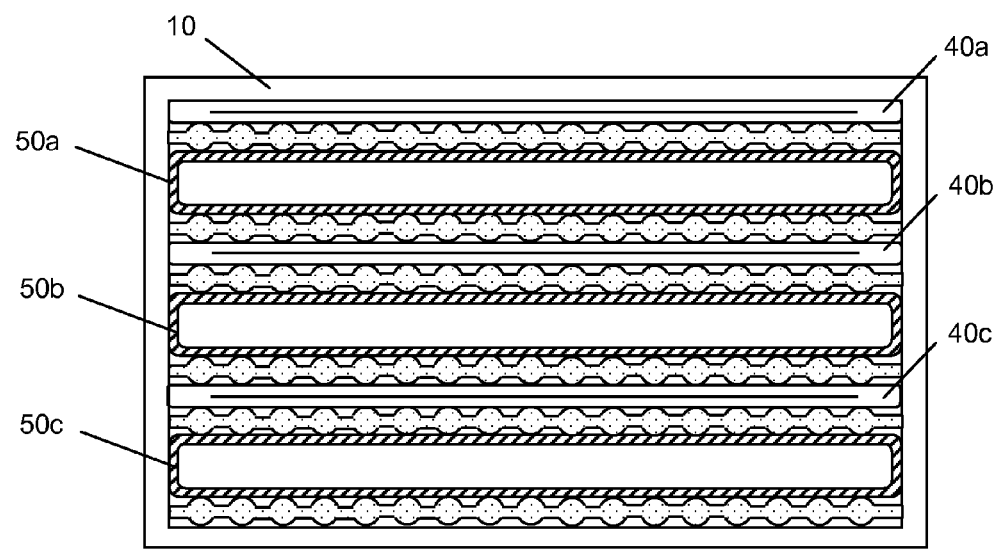

Referring now to FIGS. 5A-B, schematic cross-sections of a representative cell culture apparatus that includes a plurality of bladders 40*a-c* and bags 50*a-c* are shown. Of course any number of bladders or bags may be employed according to the teachings presented herein. In the depicted embodiment, the bags 50*a-c* are alternatingly disposed with the bladders 40*a-c* in the housing 10. That is, a bag (e.g. bag 50*b*) is disposed between two bladders (e.g., bladders 40*b* and 40*c*), and a bladder (e.g., bladder 40*b*) is disposed between two bags (e.g., bags 50*a* and 50*b*), forming a bag-bladder-bag-bladder-bag-bladder orientation. Each bag 50*a-c* is shown disposed between two spacers. However, it will be understood that no spacers, one spacer, or any number of spacers may be employed if sufficient exchange of gas between the cell culture chamber of a bag and the exterior of the bag is accomplished. The bladders 40*a-c* or bags 50*a-c* may be filled or emptied independently or in unison.

Figure 6A:
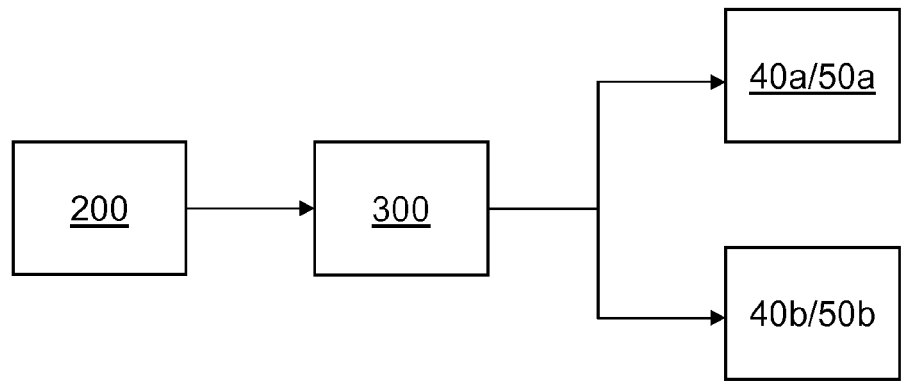
FIGS. 6A-B are schematic block diagrams of some components of a representative cell culture system.
Figure 6B:
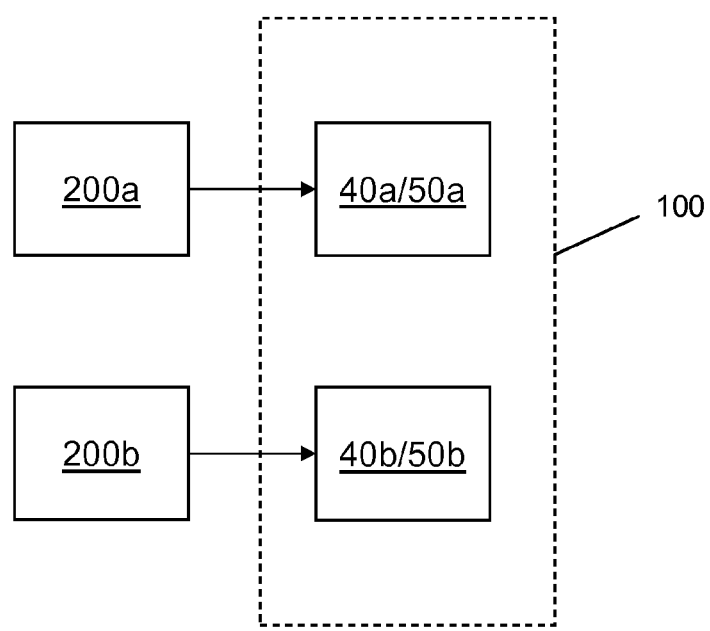

In embodiments where the cell culture apparatus includes more than one bag or bladder, the bags or bladders may be operated in unison through a manifold. For example and referring to FIG. 6A, a pump 200 may be operably coupled to two or more bladders 40*a*, 40*b* or bags 50*a*, 50*b* via a manifold 300. Of course, the manifold may be equipped with controllable valves to allow independent inflation or deflation of bladders 40*a*, 40*b* or bags 50*a*, 50*b*. Alternatively or in addition and referring to FIG. 6B, the bladders 40*a*, 40*b* or bags 50*a*, 50*b* may be filled or emptied independently. For example a first bladder 40*a* or bag 50*a* may be operably coupled to a first pump 200*a*, and a second bladder 40*a* or bag 50*a* may be operably coupled to a second pump 200*b*. Any suitable pump, such as a peristaltic pump, may be employed.

Figure 7:
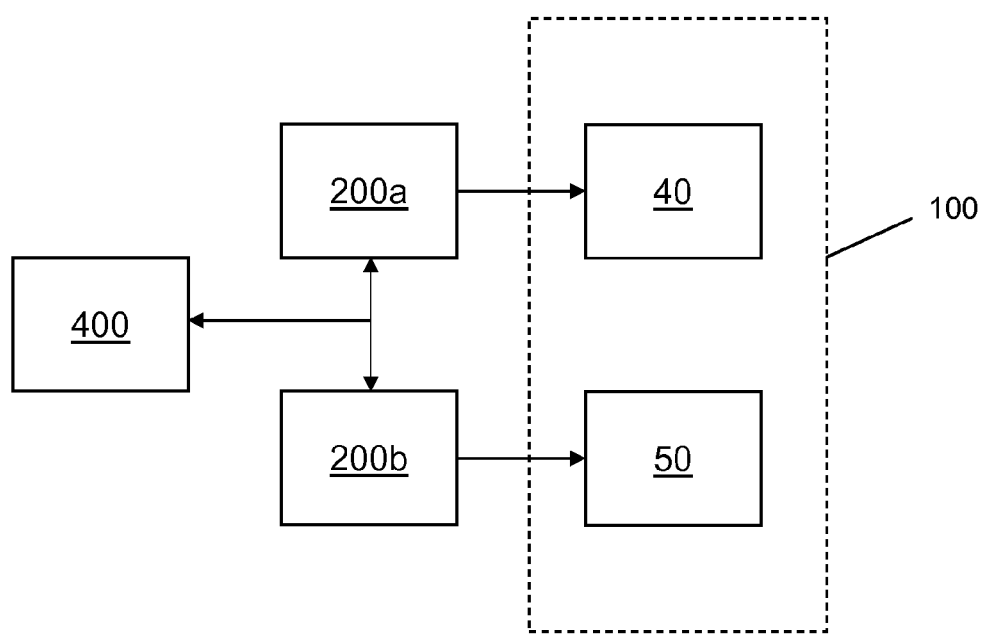
FIG. 7 is a schematic block diagram of some components of a representative cell culture system.

Referring now to FIG. 7, a controller or processor 400 may be used to control the cooperative filling and emptying of a bladder 40 and a bag 50 within a cell culture apparatus 100 as described herein. A first pump 200*a* may be operably coupled to the bladder 40 to fill and expand or empty and contract the bladder 40. A second pump 200*b* may be operably coupled to the bag 50 to insert or withdraw fluid from the cell culture bag 50. As fluid is added to or withdrawn from the bag 50, the bag 50 may expand or contract by a predictable amount, which can be readily calculated empirically or theoretically based on known properties of the bag 50. The volume of fluid added to or removed from the cell culture bag 50 by pump 200*b* may be controlled by processor 400, which may then simultaneously instruct pump 200*a* to remove a desired amount of fluid from (or add to) the bladder 40 to maintain a desired volume ratio of bag 50 to bladder 40 within the apparatus 100. The amount of fluid added or withdrawn from a bag 50 or bladder 40 may be stored in memory (not shown) accessible by processor 400. Similarly, the fluid amount to volume ratio of the bladder 40 or bag 50 may be stored in look-up tables in memory accessible by processor 400 to enable the processor or controller 400 to calculate the amount of fluid to be added or withdrawn from a bag 50 or bladder 40. A user interface (not shown), such as a keyboard or monitor, may be employed to allow a user to instruct the system with regard to the amount of fluid to be added to or withdrawn from the bag 50. The processor 400 can then determine the amount of fluid to be added to or withdrawn from the bladder 40. In various embodiments, a user may instruct the system to exert a defined amount of pressure on the bag 50. The processor 400 may then inflate (or deflate) bladder 40 sufficiently to cause the defined pressure on the bag 50. One or more pressure sensors (not shown) may be employed to provide feedback to ensure the proper amount of pressure is being applied.

Figure 8A:
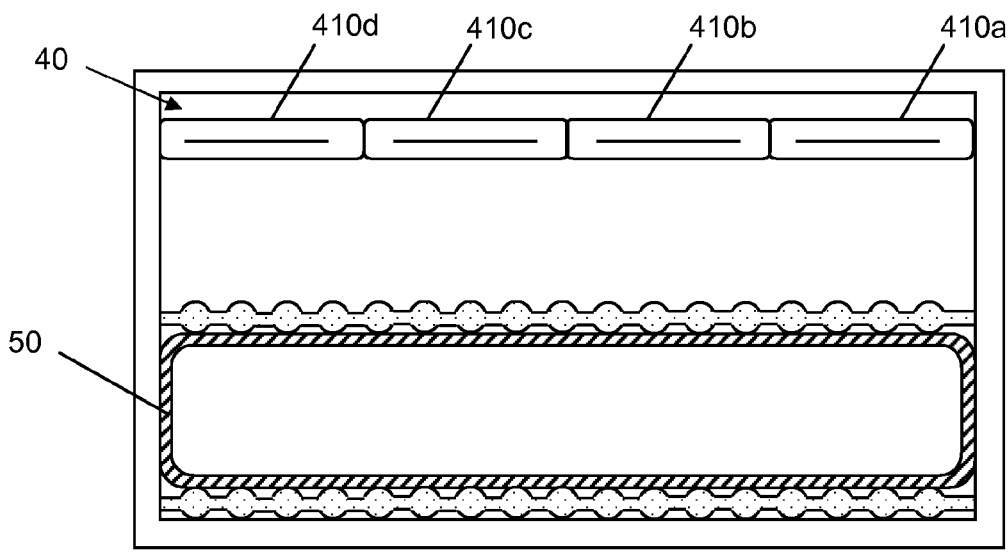
FIGS. 8A-D are schematic cross-sections of some representative components of a representative cell culture apparatus.
Figure 8B:
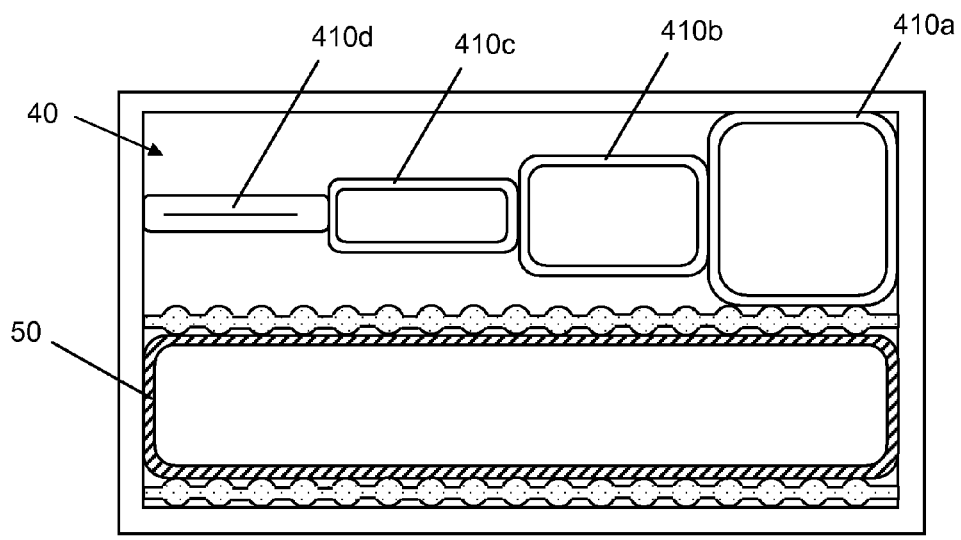
Figure 8C:
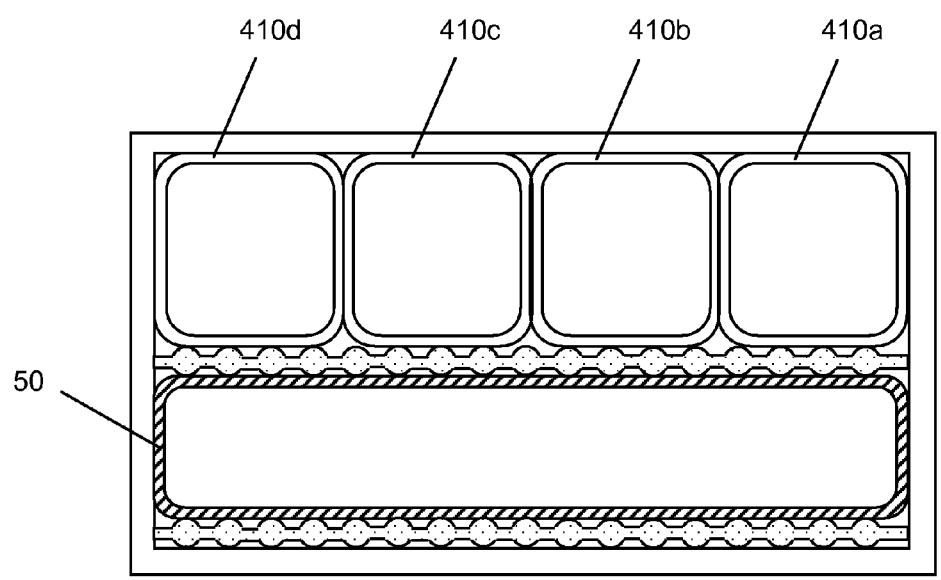
Figure 8D:
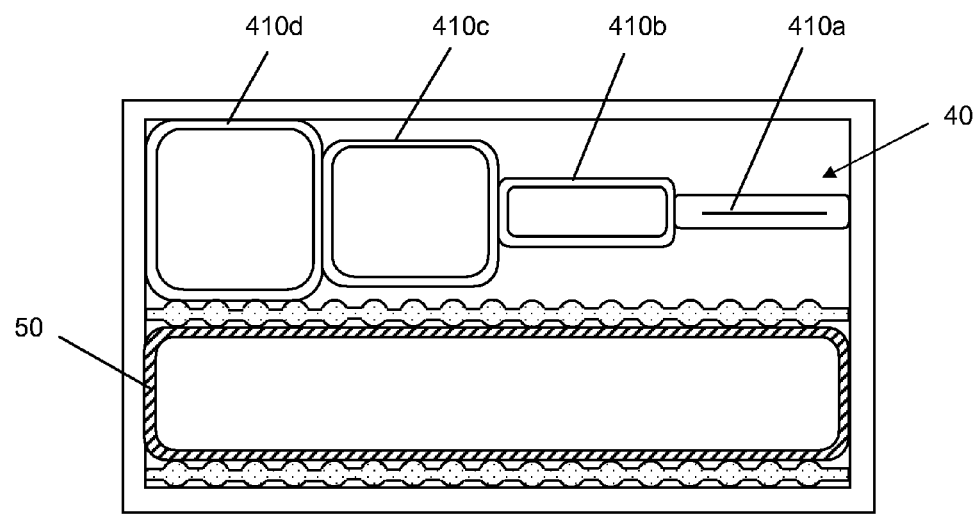

Referring now to FIGS. 8A-D, schematic cross-sections of a representative cell culture apparatus having a bladder 40 with a plurality of segments 410*a*, 410*b*, 410*c*, 410*d* is shown. The segmented bladder 40 is shown in FIG. 8A with each segment 410*a*, 410*b*, 410*c*, 410*d* being empty and contracted. In FIG. 8B, the bladder 40 is being inflated, with segment 410*a* inflated more than segment 410*b*, which his inflated more than segment 410*c*, which is more inflated than segment 410*d*. Such staged inflation may be accomplished through any suitable mechanism, such as pressure sensitive or controllable valves (not shown) fluidly disposed between the segments. Such valves may be disposed in ports (not shown) disposed between the segments of the bladder 40. In FIG. 8C, each segment 410*a*, 410*b*, 410*c*, 410*d* of the bladder is inflated to a substantially similar degree. In FIG. 8D, the bladder 40 is shown in the process of being deflated. The mechanism responsible for the staged inflation, such as pressure sensitive valves, may be employed for staged deflation. Such rolling inflation and deflation of bladder segments 410*a*, 410*b*, 410*c*, 410*d* as depicted in FIGS. 8A-D may allow for study of affects of such pressure on populations of cells cultured within cell culture bag 50. For example, the bladder segments 410*a*, 410*b*, 410*c*, 410*d* may expand and contract synchronously or asynchronously to provide the force that induces desired differentiation of the cells in culture.

While the discussion above with regard to FIGS. 8A-D was with regard to a segmented bladder, it will be understood that separate bladders, as opposed to segments of a single bladder, may be employed to accomplish a similar effect. Each of the separate bladders may be operably coupled to a separate pump or may all be coupled to a single pump via a controllable-valved manifold.

Figure 9:
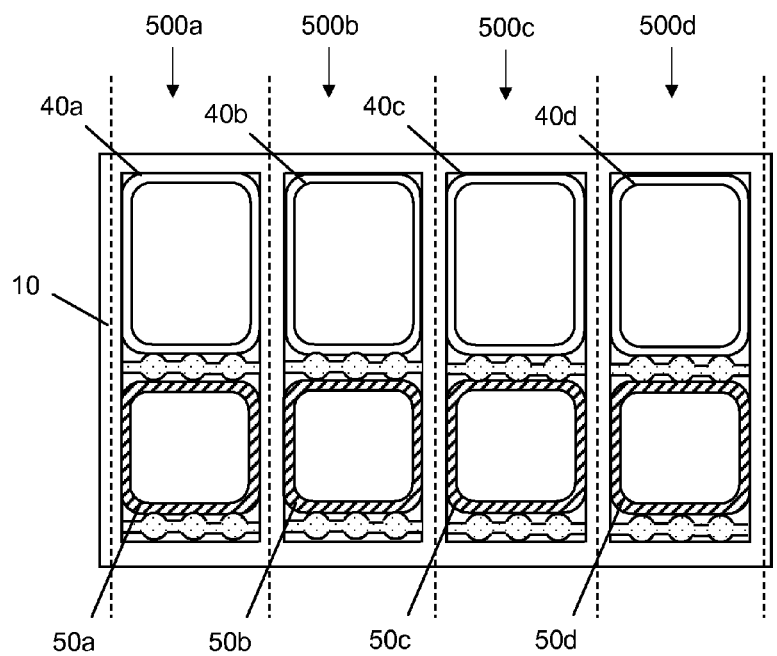
FIG. 9 is a schematic cross-section of some representative components of a representative cell culture apparatus.

Referring now to FIG. 9, a schematic cross-section of a representative cell culture apparatus is shown. The assembly includes a housing 10 defining a plurality of compartments 500a, 500b, 500c, 500d (indicated by space within housing 10 between dashed lines). Of course the compartments 500a, 500b, 500c, 500d may be formed from walls inserted into the housing 10. Within each compartment 500a, 500b, 500c, 500d, a cell culture bag 50a, 50b, 50c, 50d and a bladder 40a, 40b, 40c, 40d is disposed. Each of the bags 50a, 50b, 50c, 50d are shown disposed between two rigid shelf spacers. It will be understood that any spacer or number of spacers may be employed to allow so long as desired air exchange across the bag is achieved. The bags 50a, 50b, 50c, 50d or bladders 40a, 40b, 40c, 40d may be filled or emptied independently or in unison.

Cell culture apparatuses having a plurality of compartments, such as the apparatus depicted in FIG. 9, allow for well controlled studies of the effects of pressure applied by a bladder on cells in separately housed bags within the same cell culture apparatus.

While bladders are depicted herein as being above bags, it will be understood that in operation bladders may be disposed below bags. In some circumstances, such as when applying mechanical stress to cells cultured in bags, it may be desirable for a bladder to be located below the bag.

While each of the figures or series of figures are described herein as separate embodiments, it will be understood that the discussion with regard to a particular figure or series of figures is applicable to the discussion with regard to a different figure or series of figures Thus, embodiments of CELL CULTURE APPARATUS AND METHOD are disclosed. One skilled in the art will appreciate that the cell culture apparatuses and methods described herein can be practiced with embodiments other than those disclosed. The disclosed embodiments are presented for purposes of illustration and not limitation.

The use of numerical identifiers, such as "first", "second", "third", etc. in the claims that follow is used for purposes of identification and providing antecedent basis. Unless content clearly dictates, it should not be implied that a numerical identifier refers to the number of such elements required. For example, if a first bag forms a first chamber and a second bag forms a second chamber, it should not be implied that the second bag necessarily includes two chambers.

What is claimed is:

1. A cell culture apparatus comprising:
   a housing;
   a first bag disposed in the housing, the first bag having an exterior surface and an interior surface, wherein a first chamber for culturing cells is defined by the interior surface of the first bag;
   a first inflatable bladder disposed within the housing and external to the first bag; and
   a first spacer having a first plurality of raised features and disposed in the housing between the first bladder and the first bag, wherein the first plurality of raised features are in contact with the exterior surface of the first bag to provide a first passageway for air flow along the exterior surface of the bag between the raised features of the first plurality of raised features;
   wherein the first bladder is sufficiently inflatable and expandable to exert pressure on the first bag when the first chamber is substantially free of fluid,
   wherein the first bladder comprises first and second sequentially inflatable segments.

2. The cell culture apparatus of claim 1, wherein the first spacer comprises a rigid shelf moveable within the housing and disposed substantially along the length of the bag.

3. The cell culture apparatus of claim 1, further comprising:
   a second bag disposed in the housing, the second bag having an exterior surface and an interior surface, wherein a second chamber for culturing cells is defined by the inner surface of the second bag,
   wherein the first spacer is disposed between the exterior surface of the first bag and the exterior surface of the second bag, wherein the first spacer further comprises a second plurality of raised features in contact with the exterior surface of the second bag to provide a second passageway for flow of air along the exterior surface of the second bag between the raised features of the second plurality of raised features, and
   wherein the first bladder is configured to inflate and expand within the housing to exert pressure on the second bag when the second chamber is substantially free of fluid.

4. The cell culture apparatus of claim 3, wherein the second bag is disposed between the first spacer and the first bladder.

5. The cell culture apparatus of claim 4, further comprising:
   a second spacer disposed in the housing and between the first bladder and the second bag, wherein the wherein the second spacer has a plurality of raised features in contact with the external surface of the second bag to provide a passageway for air flow along the exterior surface of the second bag between the plurality of raised features of the second spacer.

6. The cell culture apparatus of claim 1, further comprising:
   a second inflatable bladder disposed in the housing,
   wherein the first bag is disposed between the first bladder and the second bladder, and
   wherein the second bladder is sufficiently inflatable and expandable to exert pressure on the first bag when the first chamber is substantially free of fluid.

7. The cell culture apparatus of claim 6, further comprising:
   a second spacer disposed in the housing and between the first bag and the second bladder, the second spacer having a plurality of raised features in contact with the external surface of the first bag to provide a second passageway for air flow along the first bag between the plurality of raised features of the second spacer.

8. The cell culture apparatus of claim 1, further comprising:
   a second bag disposed in the housing, the second bag having an exterior surface and an interior surface, wherein a second chamber for culturing cells is defined by the inner surface of the second bag; and
   and a second inflatable bladder disposed in the housing, wherein the second bladder is sufficiently inflatable to exert pressure on the second bag when the second chamber is substantially free of fluid.

9. The apparatus of claim 1, wherein the first and second inflatable sections of the first bladder are fluidly coupled via a pressure sensitive valve.

10. The apparatus of claim 1, wherein the interior surface of the first bag is treated or coated to facilitate culturing of cells within the bag.

11. The apparatus of claim 10, wherein the treatment comprises a treatment selected from the group consisting of plasma discharge, corona discharge, gas plasma discharge, ion bombardment, ionizing radiation, and high intensity ultraviolet light.

* * * * *